United States Patent [19]

Kitzinger et al.

[11] Patent Number: 4,845,990

[45] Date of Patent: Jul. 11, 1989

[54] ULTRASONIC MINE SURVEY PROBE

[75] Inventors: Frank Kitzinger, Montreal; Vladimir M. Labuc, Hudson, both of Canada

[73] Assignee: Noranda Inc., Toronto, Canada

[21] Appl. No.: 181,532

[22] Filed: Apr. 13, 1988

[30] Foreign Application Priority Data

May 7, 1987 [CA] Canada ............................ 536635

[51] Int. Cl.[4] ................................................ G01N 29/00
[52] U.S. Cl. ................................................ 73/597; 367/35
[58] Field of Search ............................ 73/597, 152, 151; 367/25, 27, 88, 103, 81, 86, 911, 912, 35; 181/104, 102, 101

[56] References Cited

U.S. PATENT DOCUMENTS

| | | | |
|---|---|---|---|
| 3,186,481 | 6/1965 | Foster | 73/152 |
| 3,288,210 | 11/1966 | Bryant | 73/152 |
| 3,614,891 | 10/1971 | Nolte | 181/104 |
| 4,382,290 | 5/1983 | Havira | 367/86 |
| 4,525,815 | 6/1985 | Watson | 367/912 |

Primary Examiner—Stewart J. Levy
Assistant Examiner—Louis M. Arana
Attorney, Agent, or Firm—Fleit, Jacobson, Cohn, Price, Holman & Stern

[57] ABSTRACT

An ultrasonic mine survey probe is disclosed for providing quantitative profile data in cylindrical coordinates of mine stopes, caves and other underground openings. The probe comprises a probe body adapted to be lowered at several vertical positions in an underground opening and containing a non-rotating transducer assembly adapted to generate a beam of ultrasonic energy longitudinally in the probe body, a beam focussing assembly for focussing the beam of ultrasonic energy generated by the transducer assembly, a beam reflecting device for directing the focussed beam of ultrasonic energy radially outward from the probe body toward the wall of the underground opening during transmission and to redirect the echo signals from the wall of the underground opening toward the transducer assembly. The probe body further contains means for moving the beam deflecting device at predetermined angular positions over a 360° scan range at each vertical position of the probe body, and a north orientation seeker for starting all measurement scans at the same angular direction at all vertical positions of the probe body.

5 Claims, 6 Drawing Sheets

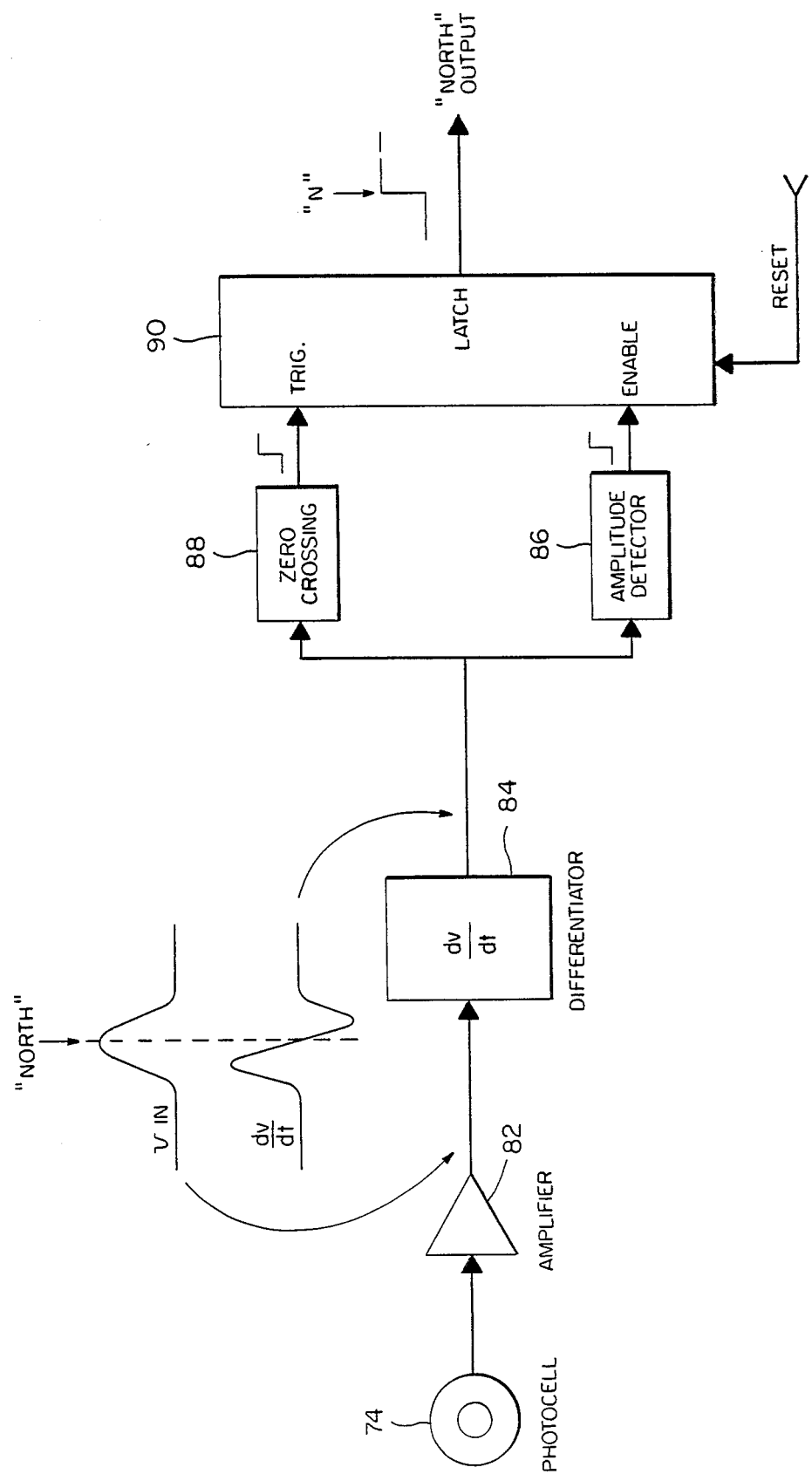

ULTRASONIC MINE SURVEY PROBE

This invention relates to an ultrasonic mine survey probe for providing quantitative dimensional profile data, in cylindrical coordinates, of mine stopes, caves, and other underground openings.

A review of available literature indicates that no instruments are presently available to remotely measure inaccessible underground openings. Current survey methods involve manual measurements, theodolites, and manual/automatic optical rangefinders. With one exception, all of the above techniques require on-site operators to perform measurements and record the data obtained.

An automatic profile measuring instrument, based on optical principles, the A. MT. PROFIL 84 (AMBERG MEASURING TECHNIQUE LTD., ZURICH), uses the method of triangulation to derive distance information and stores the data on a hand held computer. The device, however, is designed to operate mounted on a tripod base and requires manual setup at each measurement location. The tripod assembly is not suitable for lowering into inaccessible locations especially in the case where the only access to the measurement area is through small diameter (4–6″) boreholes.

It is the object of the present invention to provide an instrument enabling measurements in underground opening considered hazardous and/or inaccessible to ordinary measurement methods. The instrument uses the principle of ultrasonic ranging to determine the radial distance from the probe to the target, e.g. the rock face making up the walls of the mine stope. This principle is well known and is used in borehole logging such as disclosed, for example, in Canadian Pats. Nos. 826,305 and 832,650 to detect faults or cracks in the borehole. However, such boreholes are of small diameter and filled up with liquid. The distance travelled by the ultrasonic pulses is therefore relatively short, in a liquid medium, and the predominant frequency of the acoustic pulses is in the order of 1.35 megacycles. The above probes could not be used in the present application where the medium is air, the distances travelled by the acoustic pulses up to 50 feet, and the frequency of the acoustic pulses in the order of 50 kilocycles. More particularly, the acoustic beam needs to be sharply focussed so as to narrow the free air transducer bandwidth to approximately 8° to increase the target resolvability, thus requiring the use of a beam focussing assembly at the output of the transmitter. This cannot be done with rotary transmitters and receivers such as used in conventional borehole logging which radiate outward from the probe body without unduly increasing the diameter of the probe. Another drawback of the probes used in borehole logging is that they use rotating scanners, photo-cells and other measuring instruments, which require slip rings to feed to or detect signals from such instruments. The use of slip rings is objectionable because they generate electrical noise and are subject to wear.

The ultrasonic mine survey probe, in accordance with the present invention, comprises a probe body adapted to be lowered at several vertical positions in an underground opening, a non-rotating transducer assembly mounted in the probe body and adapted to generate a beam of ultrasonic energy longitudinally in the probe body, a beam focussing assembly mounted in the probe body for focussing the beam of ultrasonic energy generated by said transducer assembly, a beam reflecting device mounted in the probe body for directing the focusses beam of ultrasonic energy radially outward from the probe body toward the wall of the underground opening during transmission and to redirect the echo signals from the wall of the underground opening toward the transducer assembly, driving means for moving the beam deflecting device at predetermined angular positions over a 360° scan range at each vertical position of the probe body an a north orientation seeker also mounted in the probe body for starting all measurement scans at the same angular direction at all vertical positions of the probe body.

Transmitting the ultrasonic acoustic beam longitudinally in the probe allows beam focussing within the probe without increasing the diameter of the probe. This permits construction of a small diameter probe allowing lowering of the probe through boreholes to remotely map inaccessible and/or hazardous underground openings in three dimensions.

Another aspect of the present invention is that the transducer assembly is stationary in the probe thus rendering the instrument less susceptible to electrical noise. Scanning is performed by rotating the beam deflector instead of the transducers themselves.

A crucial aspect of performing meaningful measurements is to reference the starting point of all measurement scans to the same angular direction at all vertical positions. Referencing to the earth's magnetic north direction was chosen for use in the survey probe because of its inherent simplicity and reliability. Random orientation devices such as gyroscope based devices are delicate and usually cost prohibitive. Commercially available electronic north seeking devices although cheaper than gyroscopic instruments, are still relatively expensive, and would constitute a sizable fraction of the cost of the complete instrument. A novel, inexpensive, method of establishing north orientation using an ordinary magnetic compass was developed for use in the survey probe and comprises a photocell which is secured to the probe body, a slotted disc acting as an optical mask for the photocell coupled to the beam driving means, a magnetic compass spaced from said beam driving means and having its north pointer painted optically white, an illumination source located above the compass, means responsive to the illumination source to form an image of the compass north pointer onto the photocell through the slotted disc to allow the photocell to generate an output signal at the time the beam reflecting device is pointing northward so as to start all measurement scans at the same angular direction at all vertical positions.

It will be noted that the photocell is stationary in the probe thereby rendering the instrument less susceptible to electrical noise.

The probe preferably comprises an electronic circuit for processing the signals generated by the photocell. The electronic circuit comprises a differentiator circuit whose output is proportional to the slope of the output signal generated by the photocell, a zero-crossing trigger and a signal amplitude detector connected to the differentiator circuit, and a bistable latch responsive to the zero-crossing trigger and the amplitude detector for providing an output pulse for starting all measurement scans at the exact angle of north orientation.

The transducer assembly preferably comprises a transducer mounted at the lower end of the probe and adapted to transmit ultrasonic energy toward the bottom of the underground opening to provide an indication of the distance to the bottom of the underground opening. The invention will now be disclosed, by way of example, with reference to the accompying drawings in which.

Figure 1:
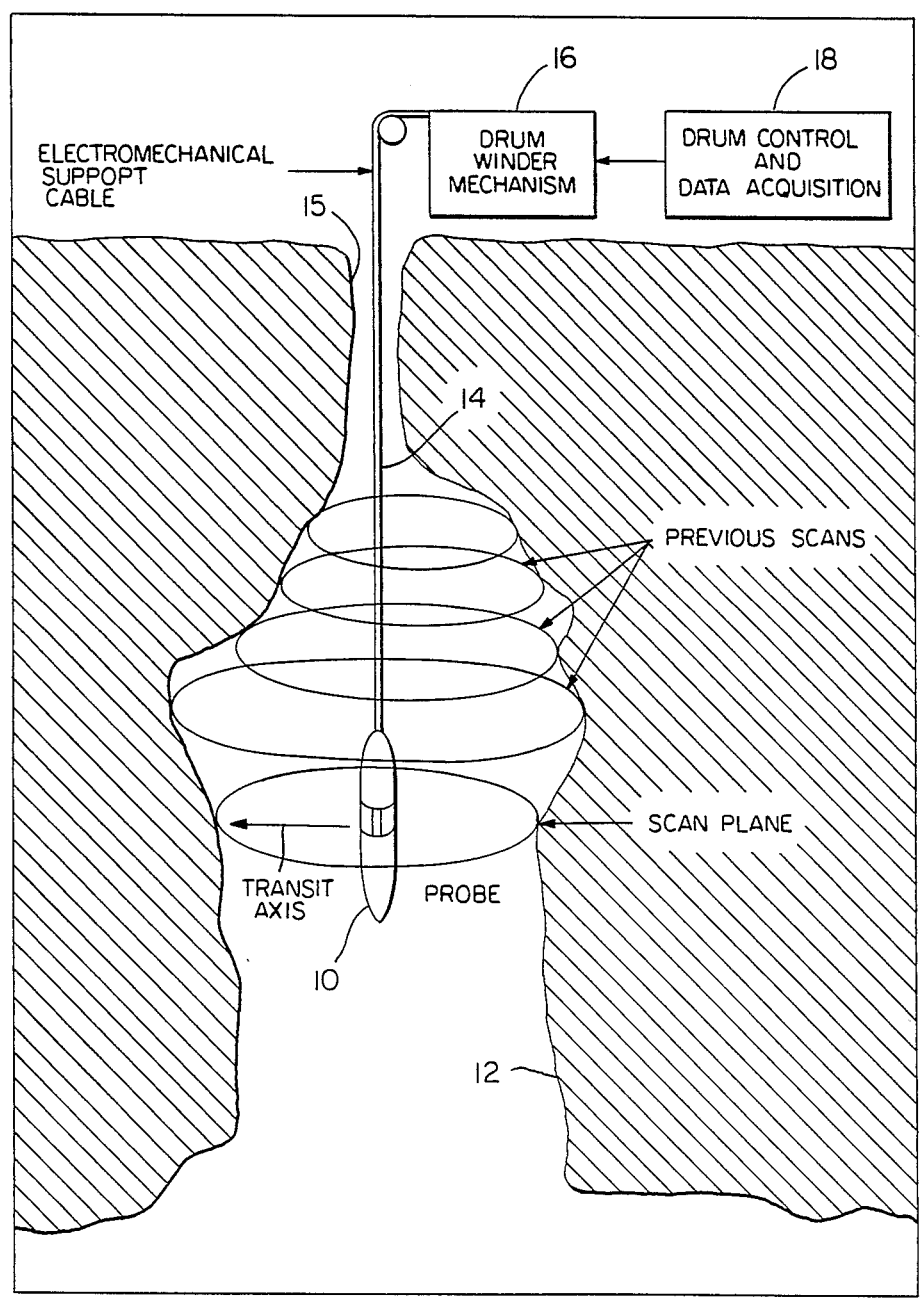
FIG. 1 is a sketch illustrating the survey probe suspended inside a stope cavity.

FIG. 6 is a block diagram of the electronics of the north seeker assembly. Referring to FIG. 1, the ultrasonic mine survey system comprises a measurement probe 10 suspended inside a stope 12 by an electromechanical support cable 14 passing through a small diameter borehole 15. The support cable is lowered by a drum winder mechanism 16 under the control of a digital control and data acquisition system 18. The electromechanical support cable contains individual conductors for transfer of power, control signals and measurement of data between the probe and the digital control and data acquisition system. In operation, the digital control and data acquisition system energizes the drum winder and lowers the probe to a plurality of vertical positions inside the stope. A measurement "scan" is generated by the probe at each vertical position by transmitting a beam of ultrasonic acoustic energy at predetermined angular positions over a 360° scan range and converting the echo signals reflected from the wall of the stope into electrical echo time pulses representative of the distance of the probe from the wall of the stope. The echo time pulses for each angular position of the beam are transmitted via the electrical conductors forming part of the support cable to the data acquisition system. A complete set of radial distance readings within the scan plane constitutes a control profile of the inner circumference of the stope wall at the indicated vertical measurement point. The angle between each distance reading can be varied to suit individual measurement resolution requirements and would typically vary between 10 and 100 steps per 360° of rotation. A set of contour scans over the total vertical measurement distance constitutes a three dimensional representation of the mapped cavity. Information regarding vertical position, measurement angle, and radial distance pertaining to that angle is stored in an ordered sequence in the data acquisition system and can be retrieved for display or further processing.

Figure 2:
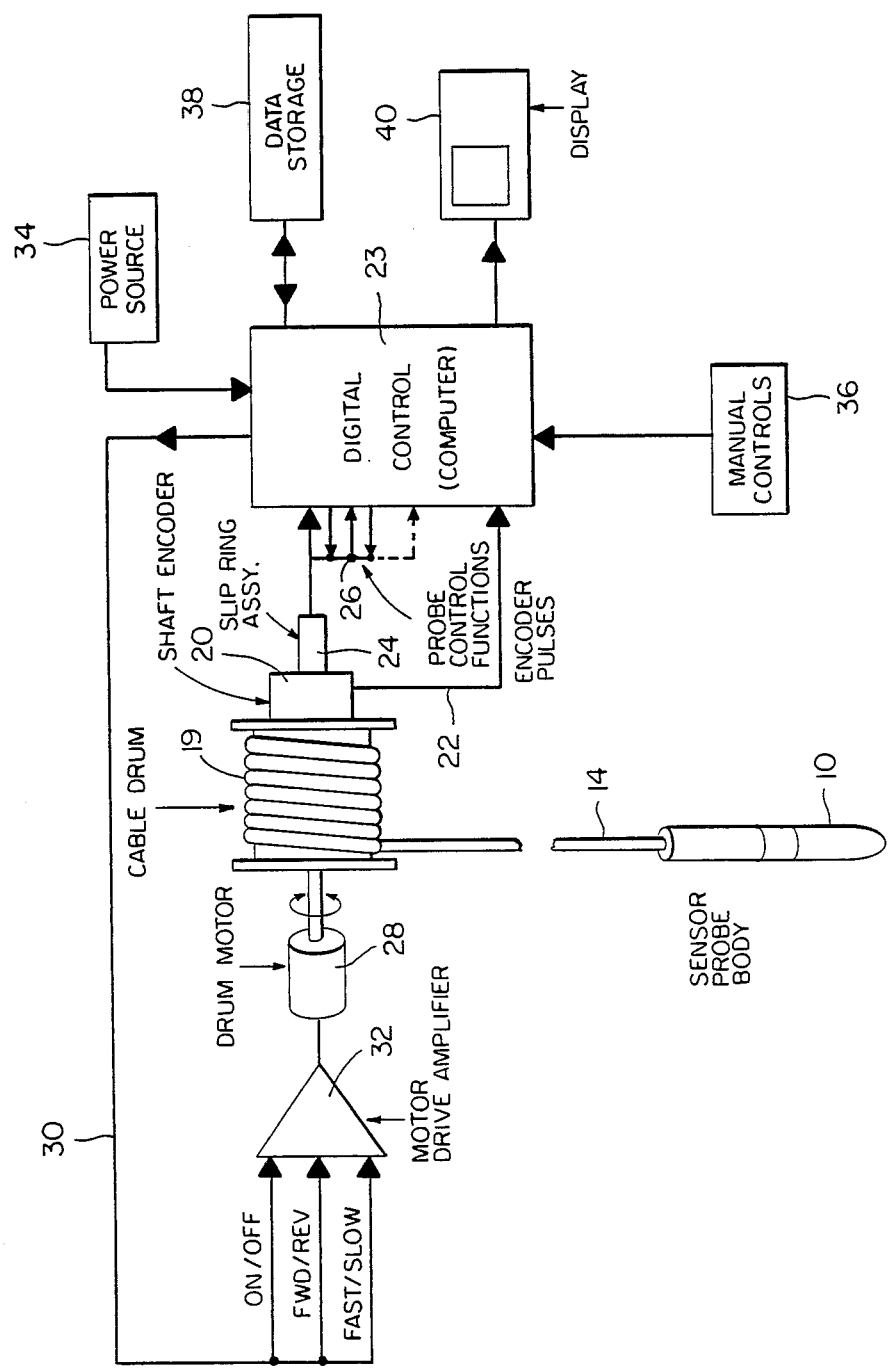
FIG. 2 is a block diagram of an ultrasonic mine survey system utilizing a probe in accordance with the present invention.

A block diagram of the digital control and data acquisition system and of the drum winder winch mechanism can be seen in FIG. 2. The probe 10 which is suspended by means of armored electrical cable 14 is wound as one layer on an electrically operated drum 19. The single layer design allows measurement of cable length payout and take-up by directly monitoring drum rotation. A standard optical-based bidirectional shaft encoder 20 is used to provide cable length (vertical distance) information, and interfaces directly through conductors 22 with a digital control system 23. The individual wires in the interior of the support cable are terminated, at the winder end, by a set of off-the-shelf slip rings 24, one half of which rotates with the drum. The stationary half of the slip rings couples to the digital control system through conductors 26 and is used to couple signals and power to the probe. A DC motor 28, driven by digital control signals transmitted over conductors 30 to a motor drive amplifier 32, operates the winch and uses standard power switching techniques to generate on/off, forward/reverse, and fast/slow operation. Power for the digital control system is obtained from a standard source 34 consisting of 12 V DC rechargeable batteries to enable portable operation. AC line supplies can also be used where applicable.

The digital control system 23 may be an off-the-shelf computer which uses known technology to store operating program and measurement data. All instrument functions are controlled by the computer, with manual controlls 36 provided for system check out and program modifications. In general, any suitable control system with sufficient data storage capability as illustrated by block 38 can be used. On site data (contour profile) presentation may be provided via a built-in display 40.

Figure 3:
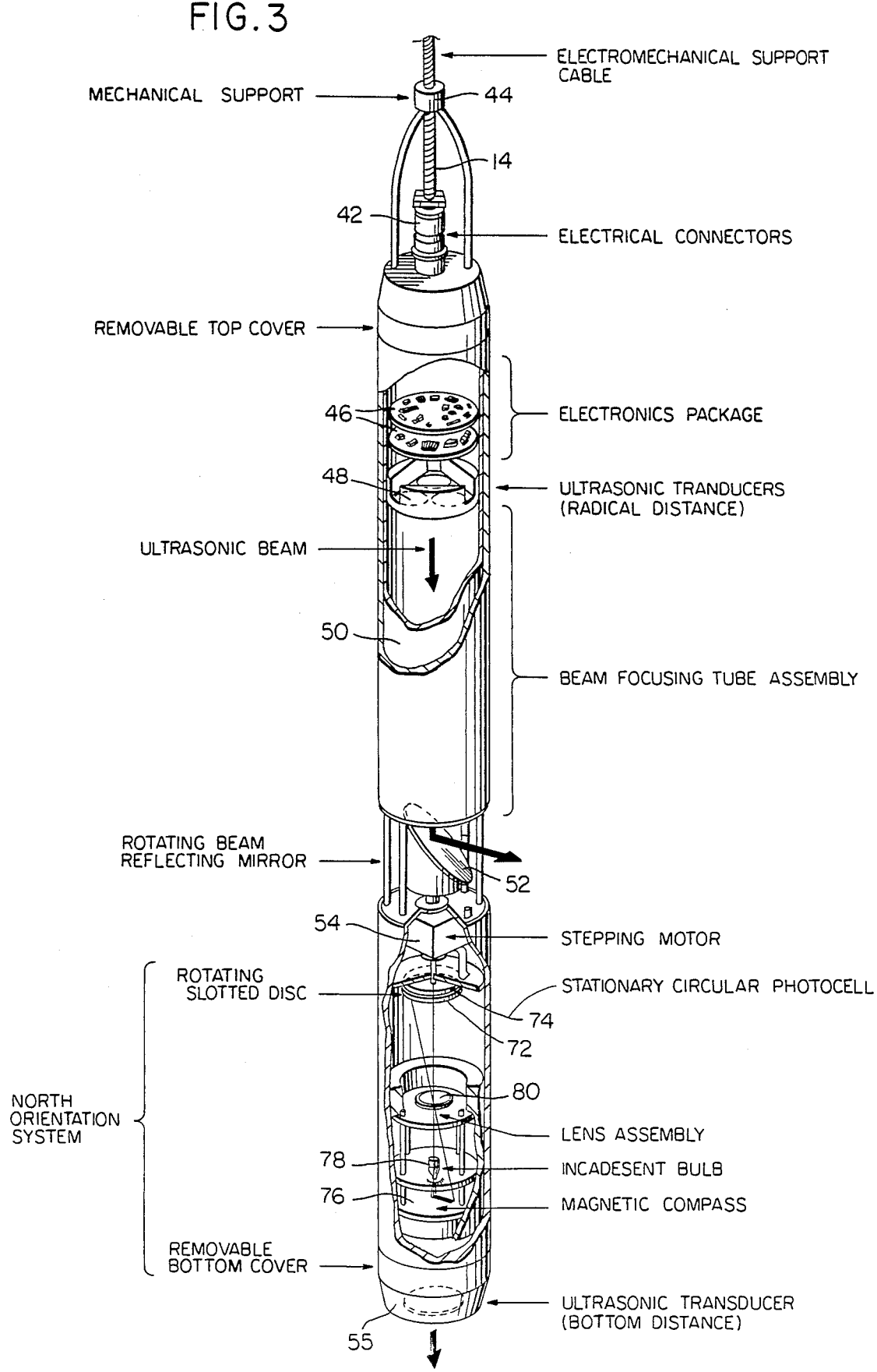
FIG. 3 is a view of the survey probe in accordance with the present invention.

A view showing the essential components of the probe can be seen in FIG. 3. The support cable is terminated in an electrical connector 42 and a mechanical support 44 at the top of the probe. An electronics package 46 is mounted directly below the connector and provides the necessary circuitry to drive the stepping motor, control the ultrasonic transducer functions, and to process the signals from the north seeker system as it will be disclosed later.

A main transducer assembly which performs the radial distance measurement function is located below the electronics package. The transducer devices are commercially available from Polaroid Corporation, which sells the units on a component basis. In the survey probe, three such devices 48 are mounted in a triangular plane pattern. The three units are driven in phase by separate amplifiers, as it will be seen later in the description of FIG. 4, which serves to effectively triple the available transmit power over that obtainable with a single unit. The transmitted ultrasonic beam travels down a beam focussing tube 50 assembly, which consists of the hollow probe body which is lined with a thin sound absorbing material layer. The focussing tube serves to narrow the free air transducer beamwidth of 30° to approximately 8° thereby increasing target resolvability. The focussed ultrasonic beam is reflected toward a target surface by a reflecting mirror 52 driven by a stepping motor 54 which is energized from the electronics package 46 under the control of the digital control system 23. The mirror is simply a metal surface inclined at a 45° angle with respect to the focussing tube. Sound waves impinging on the reflector are directed radially outward from the probe body axis during transmission and echo signals from the target are bounced back upward toward the transducer assembly which acts as a microphone in receive mode. The mirror can be constructed using any suitable acoustically non-absorbing surface. Rotation of the surface by the stepping motor serves to direct the beam over the 360° scan angle range.

A single ultrasonic transducer 55 is located at the bottom of the probe body. Its function is to provide a short range (0–10 ft typ.) indication of distance to the bottom of the opening being measured. This acts as a safety feature which gives warning to the digital control system during probe lowering. Sudden impacts against the bottom of the stope or other unforseen obstacles are thus avoided.

Figure 4:
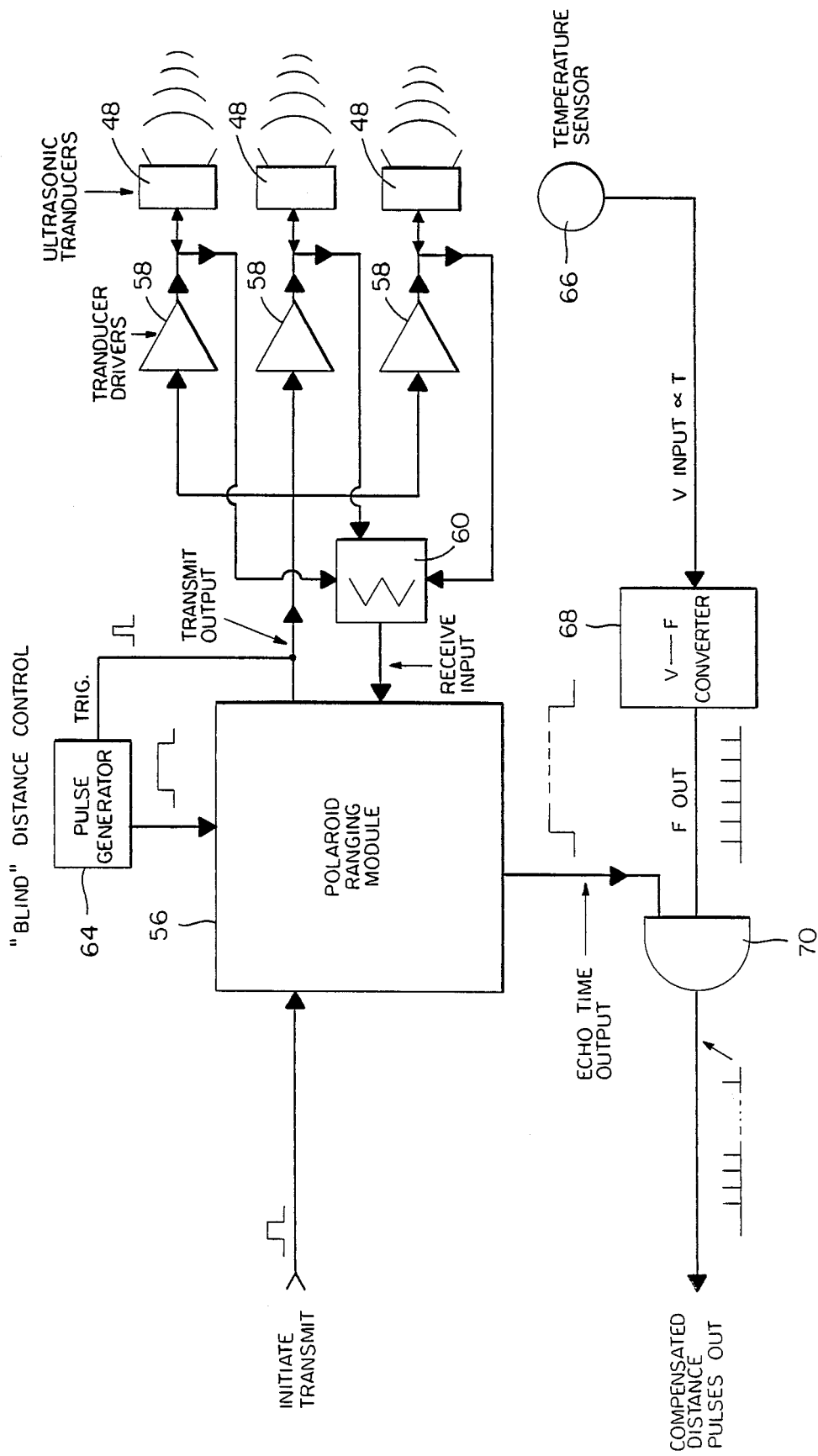
FIG. 4 is a block diagram of the ultrasonic ranging system of the survey probe.

A block diagram of the necessary functions required to perform the ultrasonic ranging operations can be seen in FIG. 4. The digital control system 23 provides an "initiate transmit" pulse which triggers a ranging module 56 which in turn provides a signal to the transducer driver amplifiers 58. The signal consists of a 1 millisecond burst at a frequency of 50 k Hz. The output of the drivers is fed to the individual transducers which convert the electrical energy into an acoustic impulse of the same frequency. In receive mode, echo signals are converted to electrical impulses by the same transducers, summed up by summing device 60, and fed to the receive input of the ranging module.

The ranging module is an off-the-shelf printed circuit assembly provided by Polaroid Corporation and is designed to operate in conjunction with the transducers made by the same manufacturer. The module is sold on a component basis and is available for general industrial use. The design of the ranging system is not limited to this particular module and any suitable system which provides the necessary amplification and detection functions can be used. The individual integrated circuits which comprise the critical circuit functions of the module are available as a standard item from Texas Instruments Incorporated. The Polaroid module represents a convenient method of implementing the necessary functions.

The "echo time" output of the ranging module 56 is triggered into a high state by the transmit pulse and is brought low again when an echo is detected or a maximum length of time has elapsed. As shipped, the ranging module is capable of measuring distances of up to 35 ft maximum, and the echo time output is brought low after the equivalent time corresponding to a two way travel of 35 ft has elapsed, whether or not an actual echo pulse is received. A modification allowing radial distances of up to 55 ft to be measured is suggested by the manufacturer and was implemented to keep the internal amplifiers active past the original 35 ft timing limit. In order to eliminate unwanted near-field echoes such as those obtained from scattered reflections at the focussing tube and reflecting mirror a "blind distance" circuit is used to disable the ranging module's detection circuit for a brief period corresponding to a distance of approximately 1 ft from the probe body. An ordinary timing circuit 64 triggered by the transmit pulse performs the necessary function.

Speed of sound versus ambient temperature compensation is performed by a solid state temperature sensor 66, located near the reflecting mirror 52, which feeds a voltage to frequency converter 68. Increasing temperature causes a proportional increase in output frequency at the converter output which provides a digital square wave drive to one input of a two input AND gate 70. The remaining input is driven by the output of the "ocho time" circuit in the ranging module. What results at the output of the AND gate 70 is a pulse train whose duration is proportional to the echo time. The actual number of pulses obtained at the output is proportional to the target distance. For a constant target distance and increasing ambient temperature, the sound velocity tends to increase thereby tending to shorten the apparent echo time. Since increasing temperature causes an increasing frequency at the output of the voltage to frequency converter the actual number of pulses contained in the time shortened pulse train will remain the same if proper calibration is assumed.

The ranging system for the distance-to-bottom sensor is identical in principle with the exception that only a single transducer is required.

Figure 5:
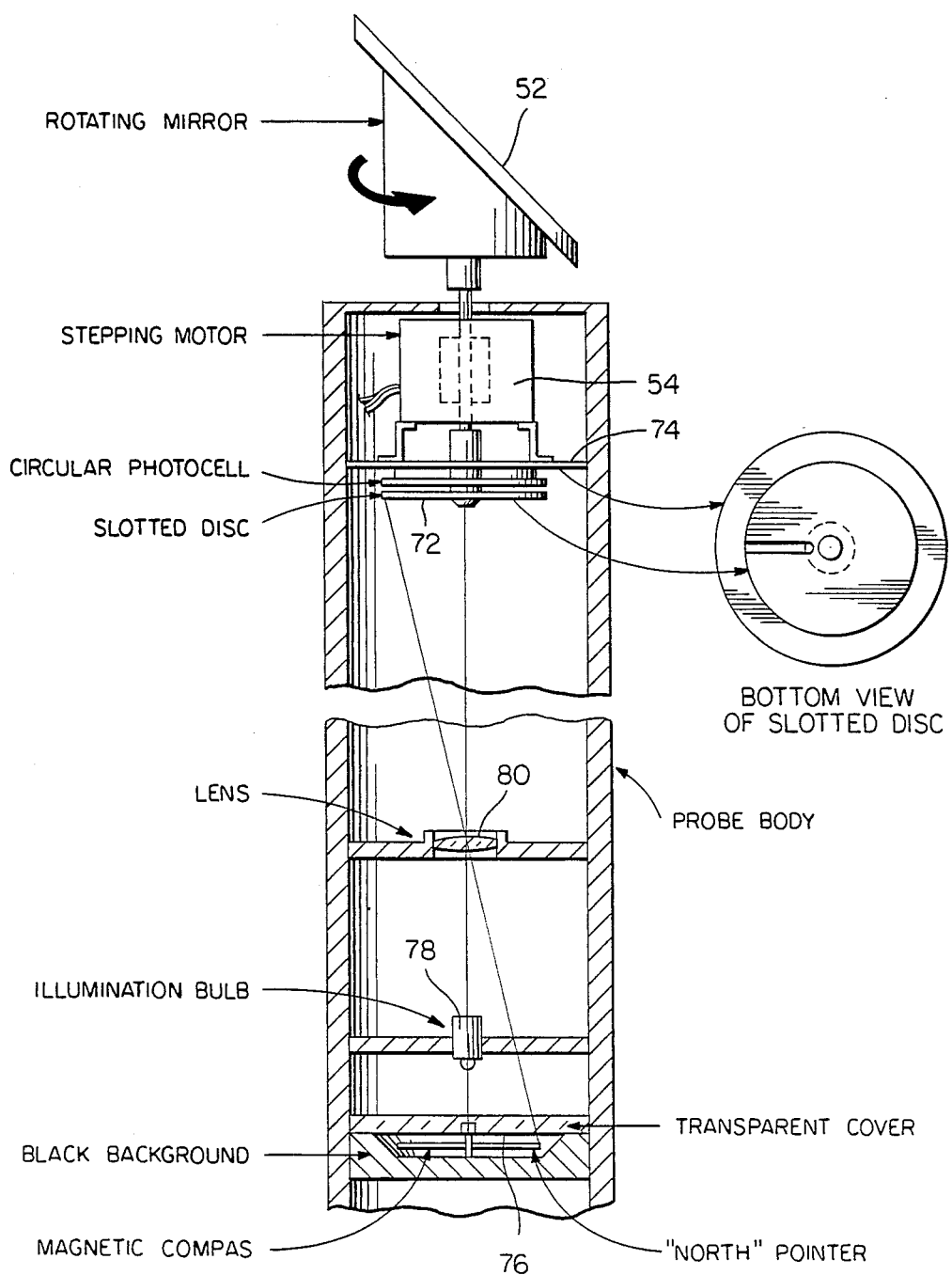
FIG. 5 is an enlarged view of the north seeker assembly of the probe.

Referring back to FIG. 3, a north orientation system is located in the bottom section of the probe. An expanded drawing of the mechanism is also shown in FIG. 5. The stepping motor 54 which drives the ultrasonic mirror 52 has a double ended shaft which extends through the top and bottom of the motor. The top end is coupled to the mirror and the bottom extension rotates a thin slotted disc 72 acting as an optical mask for a circular photocell 74 fixed with respect to the motor and sonde body. The photocell has a hole machined in its center to allow the rotating motor shaft to pass through. In this version the active material of the photocell is selenium, but a silicon or other light sensitive device of similar mechanical construction can be used.

The sensor element of the north seeker assembly is a damped magnetic compass 76 which is spaced from the stepping motor 54 to prevent interference and has its north and south pointers painted optically white and black, respectively. An incandescent bulb 78 serves as a source of illumination and is located on the vertical axis directly above the center of the compass. An optical lens 80 is located at a suitable distance above the compass face whose purpose is to focus the image of the compass pointer onto the slotted disc coupled to the stepping motor shaft. Effectively, only the image of the north pointer is registered owing to the reflectivity of the white coating and the absorptive characteristics of the black opposite pole and similarly black background. Consider what happens if the probe body is stationary and the stepping motor is continuously rotating. The white image of the north pointer is located at a random angular position on the slotted disc. As the motor turns, eventually the slot will line up with the north needle image allowing the light rays to pass through onto the photocell surface. What results is a short signal pulse from the photocell every time the slot on the disc is aligned with the image of the north compass pointer. With suitable processing, this current pulse can be used by the digital control system 23 to stop the stepping motor 54 at the exact time that the rotating assembly is pointing northward.

The electronics needed to process the photocell signal is shown in block diagram form in FIG. 6. The output signal of the photocell 74 is amplified using a standard amplifier 82 resulting in a voltage pulse as shown. For clarity, the waveforms are depicted as those which would result if the motor were allowed to rotate continuously. The output of the photocell amplifier is fed to a differentiator circuit 84 whose output is proportional to the slope of the input waveform. It can be seen that the photocell output will be at a maximum when the slot on the rotating disc 72 is exactly aligned with the north pointer image. North detection using simple voltage level sensing would result in large errors caused by changes in illumination levels due to bulb differences and aging. Sensing of the inflection point at the top of the photocell waveform, using differentiation principles, results in a reliable detection signal independent of signal amplitude. The output of the differentiator can be seen in FIG. 6. What results is a zero-crossing of the processed waveform corresponding to the peek point of the photocell signal. Subsequent circuitry consisting of an amplitude detector 86, zero crossing trigger 88, and a bistable latch 90 provides a digital logic pulse to the digital control system 23 signifying that north orientation has been established. The amplitude detector enables the latch circuit to operate only when sufficient signal amplitude has been established and prevents erroneous triggering on random noise components. The zero crossing detector senses the output of the differentiator and triggers the latch at the exact moment of north orientation. The digital control system 23 senses the latch signal and stops the rotation of the stepping motor.

Using this technique prior to the initiation of every measurement scan results in a common reference point for each measurement cycle at various vertical distances. In practice, the digital control system 23 would initiate the north seeker function several times in succession and measure the number of stepping motor pulses required to regain north orientation. Constant sequential numbers indicate that the compass has stabilized and that the probe body is not rotating. A measurement scan would then follow.

Although the invention has been disclosed with reference to a preferred embodiment, it is to be understood that it is not limited to such embodiment and that other alternatives are envisaged within the scope of the following claims.

We claim:

1. An ultrasonic mine survey probe for providing quantitative profile data in cylindrical coordinates of mine stopes, caves and other underground openings, comprising:
   (a) a probe body adapted to be lowered at several vertical positions in an underground opening;
   (b) a non-rotating transducer assembly mounted in said probe body and adapted to generate a beam of ultrasonic energy longitudinally in said probe body;
   (c) a beam focussing assembly mounted in said probe body for focussing the beam of ultrasonic energy generated by said transducer assembly;
   (d) a beam reflecting device mounted in said probe body for directing the focussed beam of ultrasonic energy radially outward from the probe body toward the wall of said underground opening during transmission and to redirect the echo signals from the wall of the underground opening toward the transducer assembly to obtain quantitative profile data in cylindrical coordinates of the wall of said underground opening;
   (e) driving means for moving said beam reflecting device at predetermined angular positions over a 360° scan range at each vertical position of the probe body; and
   (f) a north orientation seeker also mounted in said probe body for starting all measurement scans at the same angular direction at all vertical positions of the probe body.

2. An ultrasonic probe as defined in claim 1, wherein said north orientation seeker comprises a photocell which is secured to the probe body, a slotted disc acting as an optical mask for said photocell coupled to said beam driving means, a magnetic compass spaced from said beam driving means and having its north pointer painted optically white, an illumination source located above the compass, and means responsive to said illumination source to form an image of the compass north pointer onto said photocell through the slotted disc to allow the photocell to generate an output signal at the time the beam reflecting device is pointing northward so as to start all measurement scans at the same angular direction at all vertical positions.

3. An ultrasonic mine survey system as defined in claim 2, wherein said probe further comprises an electronic circuit for processing the signals generated by said photocell, said electronic circuit comprising a differentiator circuit whose output is proportional to the slope of the output signal generated by the photocell, a zero crossing trigger and a signal amplitude detector connected to said differentiator circuit, and a bistable latch responsive to said zero-crossing trigger and said amplitude detector for providing an output pulse for starting all measurement scans at the exact moment of north orientation.

4. An ultrasonic mine survey system as defined in claim 1, further comprising a transducer assembly located at the bottom of the probe body and adapted to transmit ultrasonic energy toward the bottom of the underground opening to provide an indication of the distance to the bottom of the underground opening.

5. An ultrasonic mine survey probe for providing quantitative profile data in cylindrical coordinates of mine stopes, caves and other underground openings, comprising:
   (a) a probe body adapted to be lowered at several vertical positions in an underground opening;
   (b) a non-rotating transducer assembly mounted in said probe body and adapted to generate a beam of ultrasonic energy longitudinally in said probe body;
   (c) a beam focussing assembly mounted in said probe body for focussing the beam of ultrasonic energy generated by said transducer assembly;
   (d) a beam reflecting device mounted in said probe body for directing the focussed beam of ultrasonic energy radially outward from the probe body toward the wall of said underground opening during transmission and to redirect the echo signals from the wall of the underground opening toward the transducer assembly;
   (e) driving means for moving said beam reflecting device at predetermined angular positions over a 360° scan range at each vertical position of the probe body; and
   (f) a north orientation seeker also mounted in said probe body comprising a photocell which is secured to the probe body, a slotted disc acting as an optical mask for said photocell coupled to said beam driving means, a magnetic compass spaced from said beam driving means and having its north pointer painted optically white, an illumination source located above the compass, and means responsive to said illumination source to form an image of the compass north pointer onto said photocell through the slotted disc to allow the photocell to generate an output signal at the time the beam reflecting device is pointed northward so as to start all measurement scans at the same angular direction at all vertical positions of the probe body.

* * * * *